(12) United States Patent
Ron

(10) Patent No.: US 9,386,946 B2
(45) Date of Patent: Jul. 12, 2016

(54) URINE BAG FOR COLLECTING BODY FLUIDS

(71) Applicant: GOLOO ApS, Fredericia (DK)

(72) Inventor: Izac Ron, Fredericia (DK)

(73) Assignee: GOLOO ApS, Fredericia (DK)

( * ) Notice: Subject to any disclaimer, the term of this patent is extended or adjusted under 35 U.S.C. 154(b) by 213 days.

(21) Appl. No.: 14/044,133

(22) Filed: Oct. 2, 2013

(65) Prior Publication Data

US 2014/0094665 A1 Apr. 3, 2014

(30) Foreign Application Priority Data

Oct. 3, 2012 (DK) .................................. 2012 70601

(51) Int. Cl.
| | |
|---|---|
| *A61G 9/00* | (2006.01) |
| *A61B 5/145* | (2006.01) |
| *A61F 5/455* | (2006.01) |
| *A61B 5/20* | (2006.01) |
| *A61J 19/00* | (2006.01) |
| *B65D 17/00* | (2006.01) |
| *B65D 5/00* | (2006.01) |

(52) U.S. Cl.
CPC ............... *A61B 5/14507* (2013.01); *A61B 5/20* (2013.01); *A61F 5/4556* (2013.01); *A61G 9/006* (2013.01); *A61J 19/00* (2013.01); *A61J 2205/10* (2013.01); *B65D 5/008* (2013.01); *B65D 17/04* (2013.01)

(58) Field of Classification Search
CPC .... A61B 5/14507; A61B 5/20; A61F 5/4556; A61G 9/006; A61J 19/00; A61J 2205/10; B65D 5/2033; B65D 9/06; B65D 11/10; B65D 11/105; B65D 17/04; B65D 5/008; B65D 5/02; B65D 5/0209; B65D 5/0263; B65D 5/0227; B65D 5/0236; B65D 5/0245; B65D 5/0254; B65D 5/06
See application file for complete search history.

(56) References Cited

U.S. PATENT DOCUMENTS

| | | | | |
|---|---|---|---|---|
| 4,008,851 | A | * | 2/1977 | Hirsch ............................ 383/62 |
| 4,867,576 | A | * | 9/1989 | Boyd .............................. 383/33 |
| 5,326,576 | A | * | 7/1994 | Zuege ................ B65D 81/3469 |
| | | | | 383/120 |
| 5,385,105 | A | * | 1/1995 | Withers et al. ................. 110/346 |
| 5,457,823 | A | | 10/1995 | Mojena |
| 5,487,400 | A | * | 1/1996 | Dawkins ......................... 135/87 |
| 6,139,185 | A | * | 10/2000 | Hamilton et al. ............... 383/11 |
| 7,776,418 | B2 | * | 8/2010 | Dance et al. ................. 428/40.1 |
| 8,500,708 | B2 | | 8/2013 | Glenn |
| 2008/0179330 | A1 | * | 7/2008 | Brooks et al. ............ 220/495.08 |
| 2008/0247679 | A1 | * | 10/2008 | Dayton .................. B65D 33/25 |
| | | | | 383/33 |

(Continued)

FOREIGN PATENT DOCUMENTS

WO 2006/052800 A2 5/2006

*Primary Examiner* — Adam Marcetich
(74) *Attorney, Agent, or Firm* — David S. Safran

(57) ABSTRACT

A bag for collecting body fluids, such as urine or vomit, wherein the bag in compact condition includes a front side, a back side, a bottom and at least two side edges, where a bag opening is formed opposite the bottom. The bag includes an expandable bead arranged in or close to the bag opening to keep the bag open. The bead can have several chambers that can be inflated or expanded by a resiliently deformable material arranged in the chambers. A removable absorbing material is arranged at the bottom of the bag so that a sample of the fluid can be taken before it is absorbed. At least a part of the sides of the bag can be transparent. Identification means can be provided to enable identification of the user whose liquid has been collected. The bag and the bead can be compressed and stored in compact condition.

7 Claims, 2 Drawing Sheets

(56) References Cited

U.S. PATENT DOCUMENTS

| | | | |
|---|---|---|---|
| 2009/0134165 A1* | 5/2009 | Soto | 220/345.1 |
| 2010/0234665 A1* | 9/2010 | Soto | 588/260 |
| 2010/0306914 A1* | 12/2010 | Ron | 4/479 |
| 2011/0060297 A1 | 3/2011 | Glenn | |
| 2011/0238598 A1* | 9/2011 | Borowski et al. | 705/500 |
| 2011/0316689 A1* | 12/2011 | Reyes et al. | 340/532 |
| 2012/0063705 A1* | 3/2012 | Arcot | B65D 31/16 383/104 |
| 2012/0090248 A1* | 4/2012 | Thompson | 52/2.18 |

* cited by examiner

URINE BAG FOR COLLECTING BODY FLUIDS

BACKGROUND OF THE INVENTION

1. Field of the Invention

The present invention concerns a bag for collecting body fluids such as urine or vomit, wherein the bag in a compact condition includes a front side, a back side, a bottom and at least two side edges, where a bag opening is formed opposite the bottom.

2. Description of Related Art

Presently there is a need in the care sector for assisting immobile patients, walking-impaired or elderly persons to the toilet when they are to relieve themselves. Such persons have often difficulty in getting to the toilet in time or they need help from a nurse, a nursing assistant or other assistants to go to the toilet. Immobile persons are in need of help when relieving themselves as they cannot go to the toilet by own means. This process is sometimes time-consuming and may imply cumbersome or inconvenient working positions for the care persons. Moreover, this process involves increased danger of infection for the person concerned as well as for the care persons as the existing methods involve handling and removal of urine and faeces in an inexpedient way which may cause various infections and illnesses to both patient and care persons.

A similar need exists in connection with camping, long-term travel and the like where it is not always possible to get to a toilet in time. Today there is increased focus on reducing the risk of infection in nature by avoiding that people relieve themselves in the nature, causing a health risk for other persons in the area. Also, there is a stronger focus on reducing the danger of infection among persons who travel in areas where bad hygiene can result in rapid spreading of infections and diseases when using a toilet.

Collecting urine can be performed by a well-known urine bottle made of stiff plastic material or of glass which is closed by a lid that is squeezed or screwed onto the opening. Such urine bottles have the drawback that the urine can slosh around in the bottle in connection with handling of the bottle with the risk that urine can splash out of the bottle with resulting smell nuisances. A more suitable way of collecting urine is by using a pee bag of the trademark TravelJohn™ which includes a bag with a rigid collar or plastic, and provided inside with a super-absorbing bag that transforms the urine into a gel. This bag has the disadvantage that the collar cannot be compressed and there is a risk that the collar or the joint around the collar can break by handling and storage. Furthermore, the collar forms a small elliptical opening providing that the collar is to be positioned relatively accurately in order to avoid spillage. A urine bag from the company Gleco A/S discloses a similar solution where the bag includes two cords at the opening for closing the bag, and where a super-absorbing pad placed in the bag converts the urine into a gel. This bag has the drawback that the user has to keep the bag open by him-/herself while relieving him-/herself as the bag is not stiffened around the opening. This entails a more cumbersome handling and an increased risk of spillage.

SUMMARY OF THE INVENTION

The object of the present invention is to provide a bag which is easy and simple to keep open.

The object of the present invention is to provide a bag which can absorb the liquid in the bag.

The object of the present invention is to provide a bag which can be associated with the user in question in a simple way after use.

The object of the present invention is to provide a bag which can perform a test of the liquid in the bag.

The object of the present invention is to provide a bag which can measure the amount of liquid in the bag.

The object of the present invention is to provide a bag which can be disposed of after use in a hygienically and environmentally secure way.

The present invention provides for solving the problems of the prior art by providing a bag for collecting body fluids, such as urine or vomit, characterized in that an expandable bead is arranged close to or at the edge of the bag opening, configured to open up the bag when the bead goes from a compact condition to an expanded condition.

Hereby is achieved a simple and compact bag for collecting body fluids in the form of urine, vomit or similar from a person, wherein the bead in expanded condition is configured to reinforce or stiffen the bag opening. Hereby, the bag can be compressed such that it takes up a minimum of space when not in use. This is advantageous in hospitals, nursing homes/centres as the bags thereby can be stored directly in the wards or rooms instead of in diverse depots and sluice rooms as in the case with the well-known bedpans. The bags may advantageously be compressed and stored in a packet with a certain number of bags, where the packets are stored in the room together with other dispensable equipment such as wet wipes and the like. The care personnel can hereby readily prepare a bag instead of going and getting a bedpan or a urine bottle and clean the latter, thus saving time and minimizing the risk of infection for patients and assistants. The design of the bag makes it particularly suitable for travels and camping trips as the bag can be compressed and stored in a small bag or in a pocket.

According to an embodiment of the invention, the bead is designed as an inflatable bead including at least one inflatable chamber connected with at least one valve device.

The chambers and thereby the bead can hereby be inflated (expanded) before use such that the chambers in the bead stiffen the bag opening. This means that the bag and thereby the bead can be folded/rolled up into a compressed condition. The chambers can be formed between two bag layers and be delimited by one or more joints between the two bag layers. Instead, the chambers can be formed of an additional bag layer joined to the inner or outer surface of the bag, and where the joints delimit the chambers. The bead can advantageously include a number of chambers connected in series with each other via a passage in a joint disposed between the chambers and/or via a number of valve devices connected to one or more of the chambers. The chambers can be distributed symmetrically or asymmetrically between the front side and the back side such that a desired shape of the bag opening is achieved when the chambers are inflated. In an embodiment, the bead can include a number of chambers, e.g., two, three, four, five, six, seven or more, so that the bag opening is opened up when the chambers are inflated or expanded. At least one of these chambers may extend a distance in over the front side and the back side of the bag, whereby the front and back sides of the bag are moved away from each other when the chamber is inflated or expanded.

In a particular embodiment, the chambers may include a container in the form of a capsule or ampoule containing a gas under pressure (low pressure). The container can be designed to break when the user applies a certain pressure on the container whereby the gas will flow out into the chambers and inflate the chambers so that the bead attains its expanded condition. The container can include an activation mechanism in the form of a simple valve or mechanism configured to break the sealing of the container. The user can hereby inflate the chambers just by activating the activation mechanism whereby the gas from the container flows out into the chambers. The container and/or the chamber in which the container is disposed may instead contain a liquid and a solid, or two different liquids (e.g., an acid and a carbonate) which by mixing develop a gas (e.g., $CO_2$) which in turn inflates the chambers. The two liquids or the solid and the liquid are mixed by breaking the seal between the substances, such as known from an airbag. The valve device can hereby be omitted so that the chambers form a number of closed chambers.

According to an embodiment of the invention, the bead includes a resiliently deformable material which is configured to go from a compact condition to an expanded condition when a valve device connected to the bead is activated.

The bead can hereby be designed as a resiliently deformable material, including a plurality of open or closed cell or tunnel structures. The bead may advantageously be designed of foam plastic (also called foam rubber) such as neoprene, which can be compressed into a compact condition and which will tend to return to its original shape in an expanded condition when the pressure or underpressure is removed. The bead can be arranged in the chambers or be provided on and fastened to the inner or outer surface of the bag. The bead may be configured such that the material can only expand in one direction perpendicularly to the surface of the bag. The bead can be designed as at least one band or a ring (O-ring) which is disposed at the front side and back side of the bag and extends in parallel with the edge of the bag opening. When making the bag, the bead is provided in its compact condition, possibly by means of an underpressure generated in the chambers, after which the valve device retains the bead in this condition until the valve device is activated. The deformable material can be arranged in the chambers where the material will go from its compact condition to its expanded condition when the valve device is activated. In order to ensure sufficient reinforcement or stiffening of the bag opening, more gas can be conducted/blown into the chambers than actually needed for the material to expand such that the chambers remain in their expanded condition during use. If the material is arranged on the surface of the bag, the valve device can be designed as a removable protective layer, e.g., of plastic, that keeps the material in the compact condition until the layer is removed. Alternatively, the bead can be made of a resiliently deformable material, such as rubber (including technical or synthetic rubber), with the property that the bead can be compressed (folded) together with the rest of the bag and returned to its expanded condition as well, as the bag is opened when the valve device is opened or when the bag is put into use.

According to an embodiment of the invention, the valve device includes at least one opening connected with at least one of the chambers, and a closing device arranged close to the opening, wherein the closing device is configured to fit tightly around the opening when activated.

The valve device can be designed as a valve which is opened and/or closed manually by the user. In a simple embodiment, the valve device can be designed with an opening in the form of a hole or a movable flap formed by a slit connecting the chamber with the inner or outer surface of the bag. A closing device in the form of a flap can be arranged close to the opening so that the flap can be placed over the hole and thereby close the opening. The flap may include a layer of adhesive, e.g., glue, arranged on the surface facing the opening such that the flap can fit tightly around the opening. A removable protective layer can be placed on the adhesive layer when the bag is not in use and which is removed when the valve device is to be closed. The closing device can have a different configuration, enabling the closing device to be disposed in front of and fit tightly around the opening.

According to an embodiment of the invention, the valve device is designed as a self-closing valve configured only to conduct a gas, such as atmospheric air or carbon dioxide, into the chamber when the valve is activated.

The valve hereby provides for automatic closing of the valve such that the gas remains inside the chambers, causing the bag opening to remain open. The valve can include a flap arranged inside the chamber close to the valve opening where the pressure in the chamber presses the flap against the valve opening so that the valve is automatically closed. The valve is configured to conduct a desired gas such as atmospheric air, carbon dioxide or other suitable gas from an external source into the chambers. The gas can be supplied by means of a simple hose with a connection that fits with the valve, or just by means of a straw. The gas can be supplied by means of a manual or electrically powered pump, a cartridge in which the gas (e.g., $CO_2$) is pressurized, or another suitable source. The valve has a configuration providing that the valve can be reopened (possibly destroyed) such that the chambers can be emptied entirely or partially of gas and/or more gas can be supplied to the chambers. The amount of gas in the chambers can hereby be regulated in a simple and easy way.

According to an embodiment of the invention, an absorbing material is configured to absorb the collected body fluid and configured to be disposed at the bottom of the bag.

The body fluid in the bag can hereby be absorbed by the material disposed at the bottom of the bag so that possible splashing back or spillage can be avoided. An absorbing powder or granulate can be disposed at the bottom of the bag wherein the powder/granulate may be arranged in a liquid-permeable bag. The powder/granulate can be configured to absorb the liquid and transform the liquid into a gel or crystals that bind smell and/or bacteria to the crystals/gel. A removable absorbing means or item in the form of a padding, a gauze or a cloth, for example containing super-absorbing polymers, can be disposed at the bottom of the bag, where the means is configured to absorb the liquid and bind the smell and/or bacteria. The means or item can be removed from the bag before using the bag such that it is possible to take a sample from the collected liquid. The means can then be put back into the bag so that the liquid is absorbed. The removable absorbing means may include one or more folding lines so that the means can be folded into several layers.

According to an embodiment of the invention, in or close to the bag opening there is arranged at least one other closing device configured to close the bag opening.

The bag can hereby be closed after use so that the risk of infecting the care assistants is minimized by handling of the used bag. The bag can then be disposed of in a secure and environmentally safe way. The bag can advantageously be made of a material, e.g., plastic film, which provides for the bag to be disposed of together with common waste. The closing device can be designed as a layer of adhesive, e.g., glue, arranged on the inner surface of the bag. A removable protective layer can be disposed upon the adhesive layer, where the protective layer is removed when the bag is to be closed. It will hereby be possible to weigh and register the amount of collected body fluid over a given period of time without risk of spilling body fluid or risking splash back during handling of the bag.

According to an embodiment of the invention, at least a part of the front side and/or back side of the bag is made of a transparent material.

It is hereby possible to see the collected body fluid and thereby determine its colour and possible contents visually. This is particularly relevant if the bag is used for collecting urine where a sampling of the urine is performed. At the outer surface, the bag can be provided with one or more visual indicators in the shape of lines, possibly with text or number indications, configured to indicate the volume/amount of the collected body fluid.

According to an embodiment of the invention, the bag is prepared to receive and hold at least one analyzing unit, wherein the analyzing unit is configured to perform an analysis of the collected body fluid.

Hereby, an analysis of various substances excreted in the collected body fluid to be used in further medical analysis of the user can be performed in a simple way. At the inner surface, the bag is prepared to receive and hold (e.g., in a pocket or a holder) one or more analyzing units that may be provided in the bag either at manufacture or before use. In a simple embodiment, the analyzing unit can be designed as a number of test strips, e.g., one, two, three or more, configured to perform a test for one or more predetermined substances. The analyzing unit can be configured to test the contents of glucose, pH, blood, protein, urobilinogen, ketone substances, bilirubin, nitrite, ascorbic acid, or other substances. The test strips can be arranged in front of a transparent area/window in the bag so that it is possible to perform visual reading of the test strips. In another embodiment, the analyzing unit can be designed as an electric circuit which at least comprises a microprocessor connected to one or more sensors or measuring electrodes. The analyzing unit can advantageously be made of a material making it capable of being disposed of together with common waste. The sensors/measuring electrodes can be configured to register one or more predetermined substances in the liquid as the microprocessor is configured to process the signals from the sensors/measuring electrodes. The microprocessor can be configured to detect the amount of substances in the collected liquid over time.

According to an embodiment of the invention, at least one identification means is arranged on or in the bag.

Hereby it becomes possible to identify the user who has excreted the collected body fluid in a simple and easy way. In a simple embodiment, the identification means can be designed as a readable code in the form of a bar code, a number or letter code, or other suitable code that may be read visually or by means of a scanner configured to read the code. The readable code can be arranged on the outer surface of the bag so that the reading is performed in a simple way, possibly by means of a handheld barcode scanner. The code can be recorded in the user's medical record so that it is possible to take the bag out for later analysis. Hereby it is avoided that the user or the staff needs to write on the bag or to place a tag on the bag with the associated risk of perforating or damaging the bag. In a different embodiment, the identification means can be designed as a wireless communication module connected to the microprocessor wherein the module can communicate with another wireless communication module in a handheld apparatus or a central unit. The information for the user in question can hereby be updated or changed in an easy and simple way without the staff needing to write on the bag again after use or putting a new tag on the bag.

The invention is described in the following with reference to the accompanying drawings.

DETAILED DESCRIPTION OF THE INVENTION

In the explanation of the Figures, identical or corresponding elements will be provided with the same designations in different Figures. Therefore, no explanation of all details will be given in connection with each single Figure/embodiment.

Figure 1:
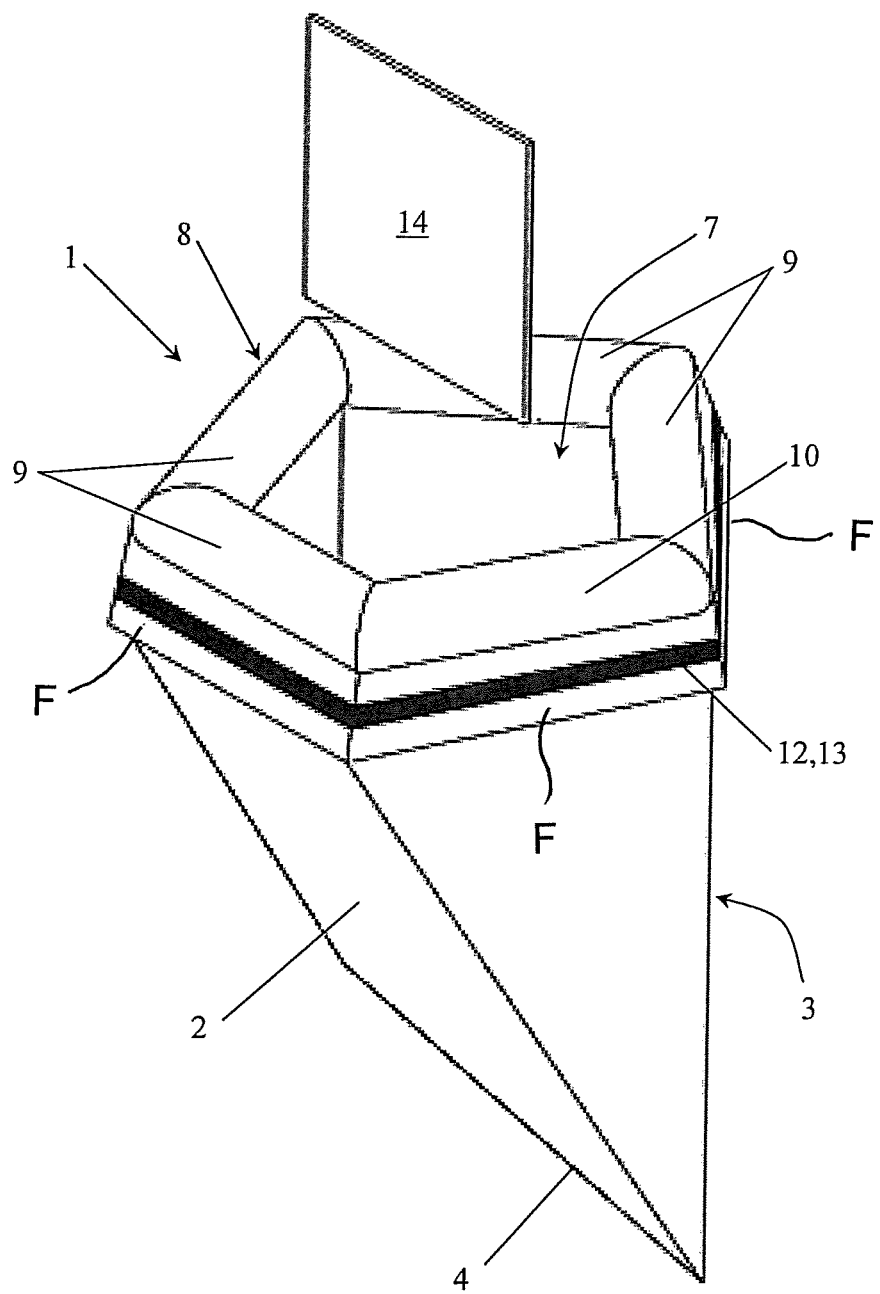
FIG. 1 shows an exemplary embodiment of a bag according to the invention with the bead in expanded condition.

FIG. 1 shows an exemplary embodiment of a bag 1 according to the invention, where the bag 1 in compacted condition includes a front side 2 and a back side 3 interconnected by a bottom 4 and at least two side edges 5, 6. The bag 1 includes a bag opening 7 disposed at the opposite end relative to the bottom 4. The bag 1 can be made of one, two or more layers of bag materials, such as plastic film which is joined at at least one of the edges 5, 6 and/or at the bottom 4. The layers of bag material may be joined at the edges 4, 5, 6 and/or the bottom by means of known jointing techniques, such as gluing, welding or other well-known jointing techniques. The front side 2 and the back side 3 include inner surfaces facing each other, and an outer surface facing away from the bag 1. The bag 1 forms an open container suited for collecting body fluids such as vomit and urine.

FIG. 1 shows the bag 1 in expanded condition where at least one expandable bead 8 can be arranged close to the edge of the bag opening 7, extending in parallel with the bag opening 7. The bead 8 can be designed as a number of inflatable chambers 9, 10 arranged at the front side 2 as well as at the back side 3 of the bag 1. The chambers 9, 10 are delimited by a number of joints between the layers in the sides 2, 3 where the chambers 9, 10 are connected in series by means of a passage 11 in the joints between the chambers 9, 10. The bead 8 can include five chambers 9, 10, of which two or more chambers can have the same length. At least one of these chambers 10 can extend a distance in over the front side 2 and the back side 3, as shown on FIG. 1, whereby the front side 2 and back side 3 are moved away from each other when the chambers are inflated. The bead 8 can be configured to form an opening area and a design providing that the bag 1 can be placed correctly on men as well as women in connection with collecting urine. The bead 8 may have a design or area providing that the bag opening 7 can be placed over both mouth and nose in connection with collecting vomit.

At least one closing device 12 can be arranged near and along the bag opening 7, wherein the closing device 12 can be disposed between the bead 8 and the edge of the bag opening 7. The closing device 12 can be disposed on the inner surface of the front side 2 and the back side 3. The closing device 12 is configured to close the bag 1 and thereby fit substantially tightly around the bag opening 7. The closing device 12 can be formed as a flap F having a layer of adhesive, e.g., glue, where a removable protective layer 13 of plastic can be disposed upon the adhesive layer 12 such that the adhesive layer 12 is protected until the protective layer 13 is removed in connection with closing of the bag 1.

After the bead 8 and thereby the chambers 9, 10 having achieved their expanded condition as shown on FIG. 1, the closing device 12 is wrung or pulled over the bead so as to avoid body fluids getting on the outer surface of the bag 1 in connection with handling of the bag 1. After use, the closing device 12 is pulled back and the protective layer 13 is removed, after which the adhesive layers 12 are moved together so that the bag opening 7 is closed. The risk of infection is therefore minimized by closing the bag 1.

At least one removable absorbing means or item 14 in the form of an absorbing pad or gauze can be provided at the bottom of the bag 1. The absorbing means 14 can be configured to absorb the collected liquid and possibly transform it into crystals or a gel. The absorbing means 14 may include a core of polymers and may be configured to bind smell and/or bacteria to the means 14. The absorbing padding/gauze 14 has a length and a width which are adapted to the internal dimensions of the bag 1. The absorbing padding/gauze 14 may include one or more folding lines (not shown) such that the padding/gauze 14 can be folded into two or more layers and thereby fit to the dimensions of the bag 1.

Figure 2:
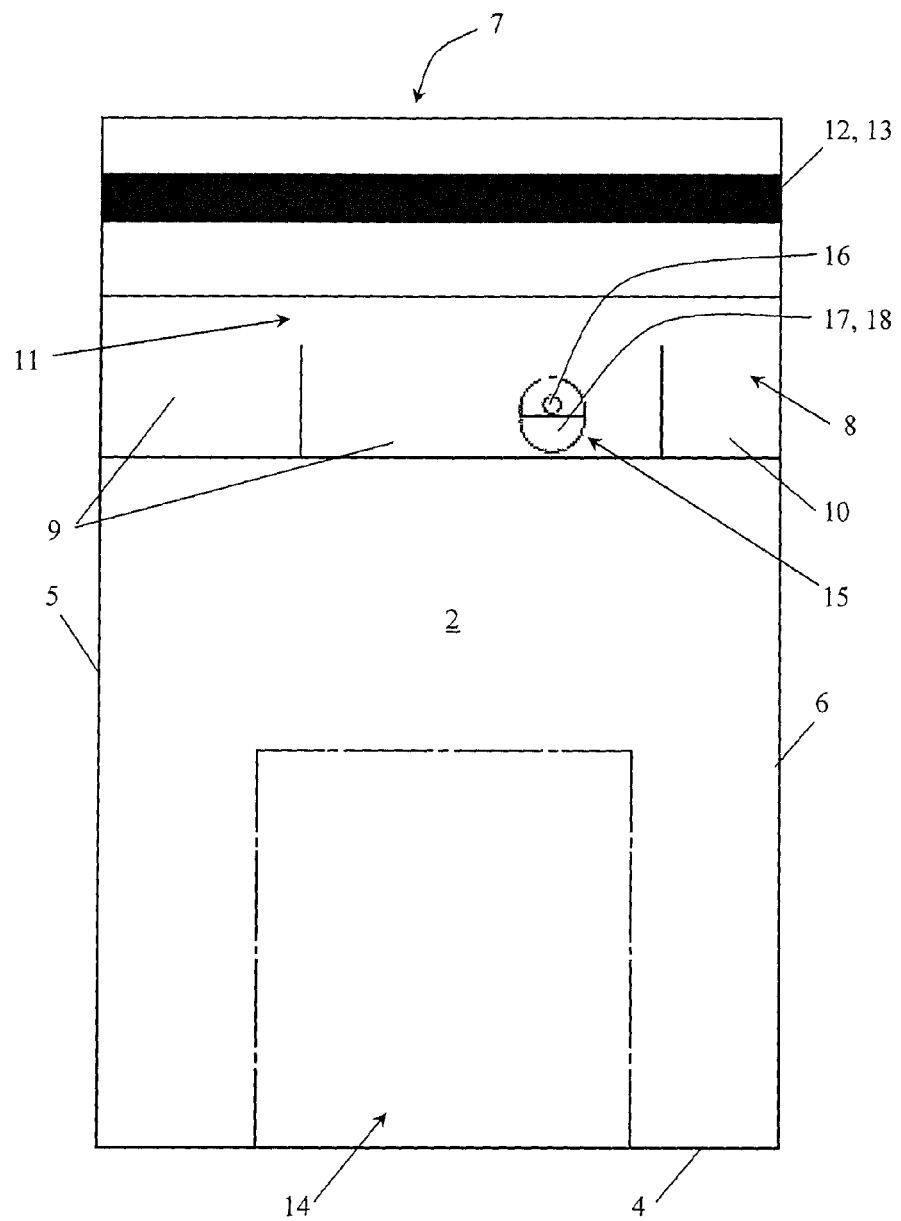
FIG. 2 shows the bag of FIG. 1 where the bead is in compact condition.

FIG. 2 shows the bag 1 in a partly compacted condition wherein the bead 8 is provided in compact condition. The chambers 9, 10 in the bead 8 can be connected to at least one valve device 15 configured at least to conduct a gas into the chambers 9, 10.

The valve device 15 can be designed as a manually activated valve which is opened and/or closed manually by the user. The valve 15 can include at least one opening 16 arranged in one of the chambers 9, 10. The opening 16 connects the chamber 9, 10, itself, with the outer surface of the bag 1 and can be designed as a hole. A closing device 17 can be arranged near the opening 16 and be configured to fit closely around the opening 16 when the closing device 17 is activated. The closing device 17 can be designed as a flap connected with the outer surface of the bag 1. The flap may include a layer of adhesive, e.g., glue, arranged on the surface of the flap facing the opening 16. A removable layer 18 of plastic can be arranged upon the adhesive layer so that the adhesive layer is protected when the bag 1 is not in use and when the bead 8 is not inflated.

When the bag 1 is put into use, the chambers 9, 10 is inflated by conducting a gas such as atmospheric air, carbon dioxide or other suitable gas into the chambers 9, 10 from an external source. The chambers 9, 10 may be inflated by means of a flexible hose (not shown) including a connection at one end, where the connection is placed in the opening 16. The user may then manually blow the gas, e.g., atmospheric air, into the chambers 9, 10 via the other end of the hose. When the chambers 9, 10 have achieved their expanded condition (inflated), the protective layer 19 is removed and the flap 17 is placed across the opening 16 so that the valve is closed. The other end of the hose can be connected to an external container where the gas is pressurized, or a manual or electric pump. The gas can then be supplied to the chambers 9, 10 by activating a valve on the container or by activating the pump.

The absorbing means or item 14 can be provided in the bag 1 during the production thereof and be stored together with the bag 1. When the bead 8 is in its compacted condition as shown on FIG. 2, the bag 1 and the absorbing means 14 can be folded or rolled up and provided in a packet (not shown). The packet can be configured to hold a predetermined number of bags 1 and absorbing means 14. Hereby, the packet and the bags 1 take up a minimum of space such that the packet can easily be stored in the patient's room or ward, or be placed in a suitcase or a backpack.

What is claimed is:

1. A body fluid bag (1) for collecting body fluids, wherein the bag in compact condition includes a front side (2), a back side (3), a bottom (4) and at least two side edges (5, 6), where a bag opening (7) is formed opposite the bottom, wherein an expandable bead (8) is arranged close to or at the edge of the bag opening (7), and at least one valve device (15) connected to the bead; wherein the bead (8) is an inflatable bead including at least one inflatable chamber (9, 10) connected with the at least one valve device (15), and wherein the bead (8) includes a resiliently deformable material which is configured to go from a compact condition to an expanded condition when the at least one valve device (15) connected to the bead is activated so as to open up the bag (1) when the bead (8) goes from the compact condition to the expanded condition, wherein at least one closure flap (F) extends from said bead and is configured to close the bag opening, the at least one closure flap being disposable on an outer surface of the bag when the bead is inflated with an adhesive closure (12, 13) facing outwardly to avoid contact with body fluids, and after use, the flap being movable to a position over the bag opening for sealing of the bag with the adhesive closure; and wherein said edge of the bag opening has a polygonal shape with said at least one flap being arranged at each side of the polygonal opening.

2. A bag (1) according to claim 1, wherein the valve device (15) includes at least one opening (16) connected with at least one of the chambers (9, 10) and a closing device (17) arranged close to the opening, where the closing device (17) is configured to fit tightly around the opening (16) when activated.

3. A bag (1) according to claim 1, wherein the valve device (15) is a self-closing valve configured only to conduct a gas into the chamber (9, 10) when the valve is activated.

4. A bag (1) according to claim 1, wherein an absorbing material (14) is configured to absorb the collected body fluid and configured to be disposed at the bottom of the bag (1).

5. A bag (1) according to claim 1, wherein at least a part of at least one of the front side (2) and back side (3) of the bag is made of a transparent material.

6. A bag (1) according to claim 1, wherein the bag (1) is prepared to receive and hold at least one analyzing unit, and wherein the analyzing unit is configured to perform an analysis of the collected body fluid.

7. A bag (1) according to claim 1, wherein at least one identification means is arranged on or in the bag (1).

* * * * *